United States Patent [19]

Dury

[11] Patent Number: 5,194,000
[45] Date of Patent: Mar. 16, 1993

[54] MANDIBULAR ENDOSTEAL IMPLANT

[76] Inventor: Georges E. Dury, Avenue Franklin Roosevelt 141, B-1050 Bruxelles, Belgium

[21] Appl. No.: 613,824

[22] Filed: Feb. 1, 1991

[30] Foreign Application Priority Data

Aug. 2, 1988 [BE] Belgium .................. 08800894

[51] Int. Cl.$^5$ .................................. A61C 8/00
[52] U.S. Cl. ................................ 433/173; 433/174
[58] Field of Search .............. 433/173, 174, 175, 176

[56] References Cited

U.S. PATENT DOCUMENTS

| | | | |
|---|---|---|---|
| 3,474,537 | 10/1969 | Christensen et al. | 32/10 |
| 3,579,831 | 5/1971 | Stevens et al. | 32/10 |
| 3,708,883 | 1/1973 | Flander | 433/174 |
| 3,732,621 | 5/1973 | Bostrom | 433/174 |
| 3,981,079 | 9/1976 | Lenczyki | 433/174 |
| 4,359,318 | 11/1982 | Gittleman | 433/173 |
| 4,431,416 | 2/1984 | Niznick | 433/174 |
| 4,547,157 | 10/1985 | Driskell | 433/173 |
| 4,645,453 | 2/1987 | Niznick | 433/173 |
| 4,738,623 | 4/1988 | Driskell | 433/173 |
| 4,789,337 | 12/1988 | Scortecci | 433/173 |
| 4,842,517 | 6/1989 | Kawahara et al. | 433/173 |
| 4,955,811 | 9/1990 | Lazzara et al. | 433/173 |
| 4,957,819 | 9/1990 | Kawahara et al. | 433/173 X |
| 4,988,297 | 1/1991 | Lazzara et al. | 433/173 |

FOREIGN PATENT DOCUMENTS

| | | |
|---|---|---|
| 0139253 | 5/1985 | European Pat. Off. . |
| 0216031 | 4/1987 | European Pat. Off. . |
| 2540077 | 4/1976 | Fed. Rep. of Germany . |
| 1211044 | 9/1958 | France ................ 433/173 |
| 2589350 | 5/1987 | France . |
| 597843 | 4/1978 | Switzerland . |
| 1373401 | 2/1988 | U.S.S.R. ................ 433/173 |

Primary Examiner—Robert P. Swiatek
Assistant Examiner—Nicholas D. Lucchesi
Attorney, Agent, or Firm—Cushman, Darby & Cushman

[57] ABSTRACT

An endosteal implant including at least one piece having a body intended to be embedded in the bone, one of the ends of which is intended to be flush with the cavity of the mouth or to be in projection in this cavity, and the dimension of which, when considered in a parallel direction to its longitudinal axis, is such that the body extends through the upper cortical area, the blueberry tissue and the lower cortical area of the bone. The body part which is intended to be embedded in the upper cortical area and to be flush with the cavity of the mouth or to be in projection in this cavity has a cross-section, when considered perpendicularly to the axis, which is lower than the corresponding cross-section of the part which is intended to be embedded in the blueberry tissue and in the lower cortical area.

25 Claims, 2 Drawing Sheets

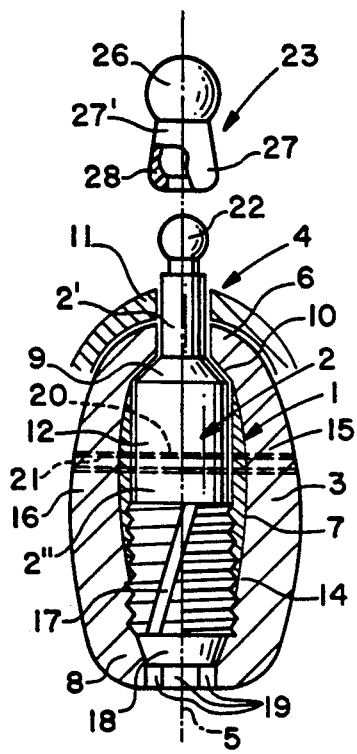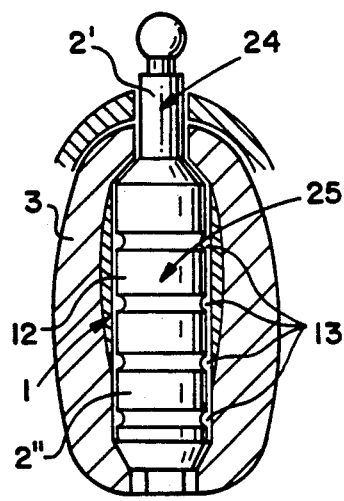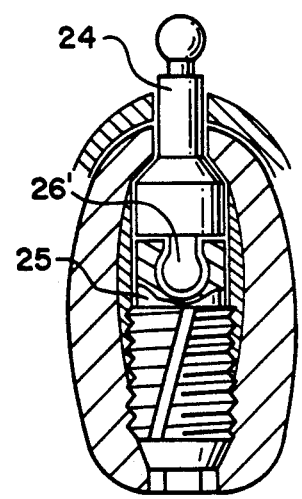
FIG. 1  FIG. 2  FIG. 3
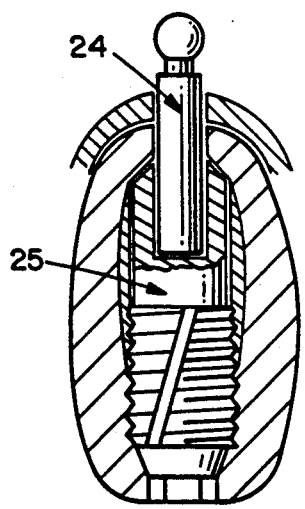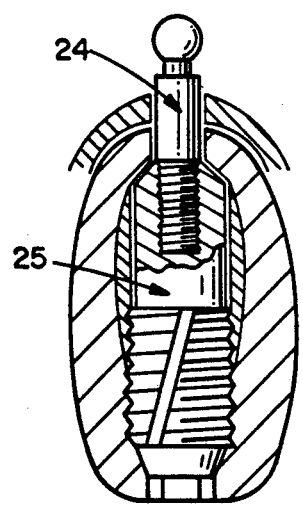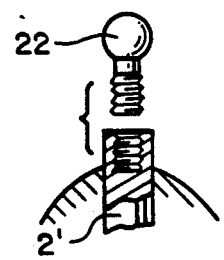
FIG. 4  FIG. 5  FIG. 6

MANDIBULAR ENDOSTEAL IMPLANT

BACKGROUND OF THE INVENTION

The present invention has for its object to provide an endosteal implant, which is used in maxillo-dental surgery, in particular surgery of the lower maxillary bone, and including of at least one piece comprising a body to be embedded in the bone, one of the ends of which is intended to be flush with the cavity of the mouth or to be in projection in this cavity and the dimension of which, when considered in a parallel direction to its longitudinal axis, is such that this body extends through the upper cortical area, the blueberry tissue and the lower cortical area of the bone in order to bear on both of these cortical areas.

Various types of known implants are in particular subdivided into two main categories, namely a first category of implants, which is certainly the most prevalent and comprises screwed or nonscrewed cylindrical implants, strip implants, and the like, which are entered, in the case of the lower maxillary bone, through the upper cortical area of the bone and extend in the latter and the blueberry tissue, and a second category of implants which are entered, again in the case of the lower maxillary bone, through the lower cortical area of the bone and extend in the latter, in the blueberry tissue and in the upper cortical area, with a subcortical plate, possibly screwed, lining the bone and through which the implants can pass.

Those implants forming part of the first category, if they are generally well biologically tolerated by the system, present, however, various drawbacks and in particular, the major drawback, on the one hand, of causing, in the case of most of them, an important traumatism of the periodontium and the fibromucosa when they are implanted, due to the fact that the realization of the flap interrupts the blood circulation and, on the other hand, of being individually relatively not very stable, due to their relatively reduced dimensions and to their simplified bioform, when they are subjected to high mechanical stresses. To reduce the risk of mobilization of the implants of this first category, it has already been thought, instead of multiplying the number thereof above four, to stabilize them either due to a surface roughness, or by associating with them some elements bearing, on the one hand, on the implants and, on the other hand, on at least one of the vestibular or lingual cortical areas of the bone. This way of proceeding, if it is already a progress, has the drawback of not using the lower cortical areas of the bone, which are by far the most resistant.

Furthermore, these prior art first category implants also present the drawback, on the one hand, of necessitating two distinct surgical interventions which are three to six months apart, the first intervention leaving the inactive implants in an embedded condition (in "nursing") and, on the other hand, of involving many manipulations using complex equipment.

Concerning the known implants of the above-mentioned second category, if they permit a surgeon to substantially improve the mechanical stability of the implant by using the lower cortical area, more particularly due to the presence of the subcortical plate, first present some drawbacks in the surgical intervention for fitting the implants, the subcortical plate and numerous screws necessary to fix in position this plate in relation with the bone. As a matter of fact, this intervention is relatively long, it presents unquestionable operative risks and can leave relatively important visible operative traces. Moreover, the plates and implants of this kind being generally made of gold alloy, their high cost which increases the drawbacks of the surgical intervention considerably limit their extensive diffusion, the latter being moreover reduced due to the relatively small number of practitioners able to carry out such interventions. In case of post-operative problems, this second category of implants makes very delicate the removal of the implants and of the subcortical plate cooperating with the latter.

Finally, the implants of both categories very often require for fixing a prosthesis the use of an external fixing element, such as a Dolder bar, cast bridge, which is in projection with respect to the gum and which binds the various implants together.

SUMMARY OF THE INVENTION

The invention has for its object to remedy these drawbacks and to provide an implant, in particular for the surgery of the lower maxillary bone (intramandibular), which allows, on the one hand, a retro and atraumatic perforation of the periodontium and of the fibromucosa and, on the other hand, due to its bioform adapted to the bone, an anchorage of the implant at least in the upper and lower cortical areas of the bone, and preferably in the cortical box formed by the lower, lingual and vestibular cortical areas, which ensures the primary immobility (at the time of positioning) and the secondary immobility (after stressing) of the implant, without necessitating laying of stabilizing elements bearing on the cortical areas, although this laying of elements is possible. The implant according to the invention also presents the important advantage of allowing, without any traumatism, the immediate epithelial rebinding and the normal collapse of the mucosa. Moreover, this implant allows, even in a limited number of two to four implants and without subcortical plate, to correctly maintain a complete prosthesis or an equivalent bridge, by suitably selecting the locations, the known implants being generally used in a larger number. Furthermore, the implant according to the invention can be successfully used in maxillary bones having a weak upper cortical area or in maxillary bone areas where the upper cortical area is substantially non-existent, for example due to recent extractions.

The implants according to the invention are easy to position with a distinctly less important surgical intervention than for fixing known implants. This intervention can be made either without cutaneous incision, or with such incisions which do not substantially cause visible scars, while being substantially without operative or postoperative risk. This type of intervention, which is made out of the cavity of the mouth can be easily carried out, due to a suitable apparatus, by any practitioner able to position simple implants of the above-mentioned screwed or non-screwed cylindrical type, without obligation, as this is always substantially the case when these latter implants are positioned, of scraping the bone in narrow projection, at the level of the upper cortical area. Furthermore, the implant according to the invention, due to the fact that it is easily and safely positioned and due to the extremely reduced number of the implants which are necessary to maintain a prosthesis, may be much more largely distributed than the known implants, taking into account the reduced cost of the implants according to the invention and of the positioning of the latter. Furthermore, their positioning necessitates only one intervention and their effectiveness may be made much quicker than the known implants, which reduces the hypodynamics, in particular by using a simple piece (which is described hereinbelow) and which allows to advantageously replace the above-mentioned external fixing means, and intended to ensure the removable or fixed attachment of the prosthesis to the implant, this piece being itself removably fixed on the implant, these fixations being of the interlock type, the interlocking on the implant being less or more resistant than the interlocking on the prosthesis depending on whether the latter is removable or is a bridge. The prosthesis can be quickly assembled with the implants due to the fact that these pieces are easily interchangeable and are selected to be less and less elastic as the bone supporting the implants restores by firmly immobilizing these implants. These pieces which are of very simple shapes and obviously in a number limited to that of the implant, are not traumatizing at the level of the gum and are easy to be maintained in a perfect cleanliness condition. The implants according to the invention permit a patient to progress from one prosthesis type to another, such as a removable prosthesis, a bridge, and the like. To this end, it is sufficient to change the type of binding piece.

It is also to be noted that the implant according to the invention can be easily removed in case of a problem. Moreover, this implant has, in its intraosseous area, such a diameter that, in this area, it can be covered, which is not the case in most known implants which are of a low cross-section, with a layer of a large enough thickness of a biomaterial able to activate the rejuvenation of the osseous material. When the implant according to the invention is used jointly with such an added piece, also according to the invention, which is used as a binding between the implant and the prosthesis, it forms an implant system leaving the implant in a motionless condition and allows some movements of the prosthesis and optionally a maximum cooperation with the mucosa on which it bears while presenting the advantage of replacing, at least partly, the four functions of the ligament which surrounds the teeth and of allowing a perfect rejuvenation of the bone. These added pieces also offer the advantage of transmitting the stimuli to the bone under the threshold which is acceptable by it.

To this end, according to the invention, the portion of the body intended, on the one hand, to be embedded in the upper cortical area of the bone and, on the other hand, to be flush with the cavity of the mouth or to be in projection in this cavity, has a cross-section, when considered perpendicularly to the longitudinal axis of the body, which is lower than the corresponding cross-section of the body portion intended to be embedded in the blueberry tissue and in the lower cortical area.

According to an embodiment of the invention, the side surface of the body, at the location where the body portion of low cross-section intended to be embedded in the upper cortical area and the body portion of larger cross-section, intended to be embedded in the blueberry tissue and in the lower cortical area fit together is shaped in order to either substantially take the shape of the internal face of the upper cortical area of the bone, or to be inserted into a corresponding cavity prepared in the upper cortical area of the bone, from its internal face.

According to an advantageous embodiment of the invention, the side surface of the body portion of low cross-section, intended to be embedded in the upper cortical area and to be flush with the cavity of the mouth or to be in projection in this cavity, is smooth.

According to a particularly advantageous embodiment of the invention, the area of the body portion of large cross-section, intended to be embedded in the lower cortical area is configured as a cylinder of revolution which is coaxial to the body, and its side face is threaded so that the nominal diameter of the thread is larger than the diameter of said body area intended to be embedded in the blueberry tissue, this threaded portion of the body extending, opposite the portion of low cross-section, as a truncated area the cross-section of which is decreasing from said threaded portion, this area having means such as cut-off flats, arranged to be used as a bearing for an instrument causing rotation of the implant around its axis in order to screw the latter into the lower cortical area or to unscrew it.

BRIEF DESCRIPTION OF THE DRAWINGS

In the Drawings

FIG. 1 is a schematical fragmentary side elevation and view, partly in longitudinal section, showing an implant according to the invention, as arranged in a lower maxillary bone provided with its piece of binding with a prosthesis, this piece being shown as being separated from the implant.

FIGS. 2 to 11 are views analogous to FIG. 1 and show some variants of the implant shown by FIG. 1.

In the various Figures, the same reference numerals designate identical or analogous elements.

DETAILED DESCRIPTION

Figure 7:
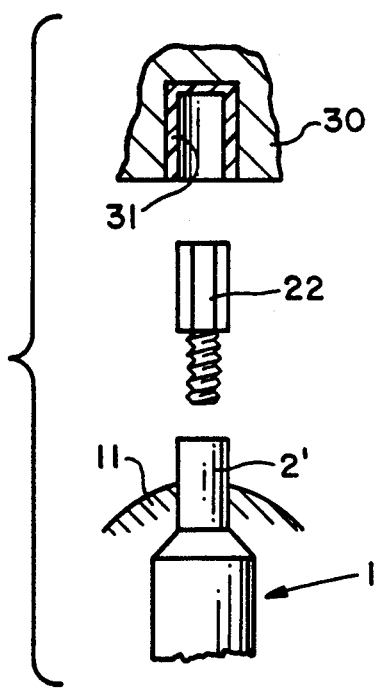

The endosteal implant 1 according to the invention and illustrated by the drawings is intended to be used in maxillo-dental surgery and in particular in surgery of the lower maxillary bone. It is formed of at least one piece comprising a body 2 intended to be embedded in the bone 3 in order that its end 4 is flush with the cavity of the mouth or is in projection in this cavity. The dimension of this body, when considered in a parallel direction to its longitudinal axis 5, is such that said body extends through the upper cortical area 6, the blueberry tissue 7 and the lower cortical area 8 of the bone, in order to bear on the two cortical areas 6 and 8. The portion 2' of the body intended, on the one hand, to be embedded in the upper cortical area 6 of the bone and, on the other hand, to be flush with the cavity of the mouth or to be in projection in this cavity, has a cross-section, when considered perpendicularly to the longitudinal axis 5 of the body, which is lower than the corresponding cross-section of the portion 2" of the body, intended to be embedded in the blueberry tissue 7 and in the lower cortical area 8. The cross-section of the portion 2' can be reduced to the minimum which is allowed for the used material and for the desired resistance without compromising for all that the general stability of the implant.

In order to reinforce the stability of the implant, the side face of the body, at the location 9 where the body portion 2' of low cross-section, intended to be embedded in the upper cortical area 6 and the body portion 2" of larger cross-section, intended to be embedded in the blueberry tissue 7 and in the lower cortical area 8, is shaped as a truncated cone so as either to substantially take the form of the internal face of the upper cortical area 6 of the bone, or, as shown by FIG. 1, to be entered into a corresponding cavity 10 made in the upper cortical area of the bone, from the internal face of the latter.

The implant which is positioned in the bone from the lower cortical area 8 allows, due to its features, an atraumatic perforation of the periodontium and of the fibromucosa. To further improve the atraumatism of the perforation and then allow the epithelial rebinding and the normal collapse of the mucosa 11, without inflammation of the latter, the body portion 2' of low cross-section intended to be embedded in the upper cortical area 6 and to be flush with the cavity of the mouth or to be in projection in this cavity is advantageously smooth. Moreover said the portion 2' of the body is configured as a cylinder of revolution having as its axis the longitudinal axis 5 of the body.

The area 12 of the body portion 2" of large cross-section, intended to be embedded in the blueberry tissue of the maxillary bone is also as a cylinder of revolution which is coaxial to the body, and its side face either is smooth or rough as illustrated by FIG. 1, or presents annular grooves 13 which are preferably regularly distributed (see FIG. 2). The area 14 of the portion 2" of the body of large cross-section, intended to be embedded at least partly in the lower cortical area 8 of the maxillary bone is configured as a cylinder of revolution which is coaxial to the body, and its side face is threaded so that the nominal diameter of the thread is larger than the diameter of the area 12 which is intended to be embedded in the blueberry tissue 7, the thread being advantageously arranged to be autotapping.

The body portion 2" of large cross-section and more particularly the area 14 of the portion 2" has a diameter which corresponds at least to the distance separating the internal faces of the vestibular cortical area 16 and of the lingual cortical area 15 of the bone and which is preferably larger than this distance. Accordingly, the implant, at least in its threaded portion, is completely inserted and supported in the very resistant cortical box, which is constituted by the lower cortical area 8, the lingual cortical area 15 and the vestibular cortical area 16.

At least one groove 17 is provided, as shown by FIG. 1, in the threaded side surface of said area 14. This groove is arranged so as to allow the bone wastes resulting from the threading of the implant through the lower cortical area 8 of the bone, to be discharged.

To reinforce the implant stability, the threaded portion of the body is extended, in order to take the shape of the cortical box and opposite the portion 2' of low cross-section, as a truncated area 18 the cross-section of which is decreasing from said threaded portion, this area 18 advantageously presenting some means, such as cut-off flats 19, which are arranged to be used as a support for an instrument for rotating the implant around its axis 5 in order to screw this implant into the lower cortical area 8 or to unscrew it.

If it is desired to more firmly block the implant in the bone, the body portion 2" of large cross-section may be provided with at least one hole (see FIG. 1) passing right through the body, along a direction perpendicular to the axis 5 of this body, and intended to receive a permanent or temporary rod 21, of corresponding cross-section, which is provided to be embedded in the bone and which is supported at least one of its ends in the vestibular cortical area 16 or the lingual cortical area 15 of the bone as a locking in a centromedullary nail in orthopedic surgery.

The implant according to the invention may be made in one piece, as shown by FIG. 1, or in two pieces, as shown in particular by FIG. 6, where the portion 22 of the implant ensuring the binding piece 23 of the prosthesis to be maintained is removable, for example by unscrewing.

Figure 8:
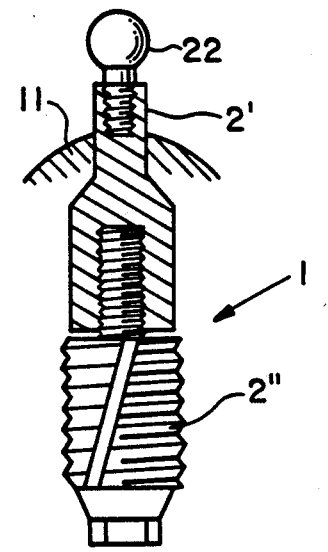
Figure 9:
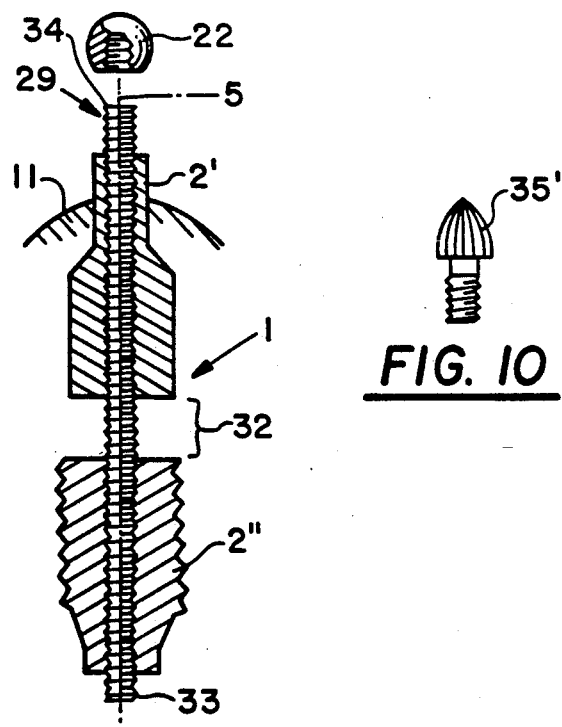

However, according to the invention, the implant body could also be made of at least two parts for some applications and as shown in particular by FIGS. 8 and 9.

Thus as shown by FIG. 2, said body 2 can include two distinct elements 24 and 25 which are abutting and freely bearing on each other, the lengths of these elements being such that their junction occurs in the blueberry tissue 7 of the bone.

As shown by FIG. 3, the body could consist of two distinct elements 24 and 25 arranged end to end and united together through a connection 26', of the knuckle type, the lengths of both elements being such that the connection 26' is located in the blueberry tissue 7 of the bone.

As illustrated by FIGS. 4 and 5, the body 2 could also comprise of two distinct elements 24 and 25 which are coaxial, the element 24 of low cross-section fitting or screwing into the element 25 of large cross-section.

The implants which are not made as only one piece have their elements which are manufactured either from a same material such as titanium, ceramic, carbon, carbonne, gold alloy, or from different materials. It could also be provided to manufacture the portion 22 of the implant, shown by FIG. 6, from a material presenting some elasticity, such as hard rubber. This portion 22 could also comprise of any screwed or cemented insert.

The insert 22 of the implant shown by FIG. 7 is particularly intended to maintain a crown or a bridge 30 on the implant 1. This crown or bridge 30 comprises a crimped visco-elastic element 31 inside which the insert 22 is lodged. As shown by FIG. 8, the implant according to the invention could also be made as three parts which are assembled by screwing, a part 2' which is forms the semi-enclosed dental implant, the part 2" which is the totally enclosed surgical implant and the insert 22, the latter screwing onto the part 2', while the latter screws onto the part 2". This implant one to control its length in proportion to the sizes of the bone. This control of length may also be obtained, in a more flexible manner, by using an implant such as shown by FIG. 9. This latter implant can be made as two parts 2' and 2" such as hereinabove defined. These parts are tapped right through, along the axis 5, and are united through a common screw 29, while allowing the control of the spacing 32 separating the pieces 2' and 2" in proportion of the corresponding dimension of the bone. When the parts 2' and 2" are in position, the portion 33 of the screw 29 which is in projection with respect to the part 2" is cut, while the portion 34 of the screw 29, which is in projection with respect to the part 2' is used as a fixing means for an insert 22 which is screwed onto this portion 34.

Figure 10:
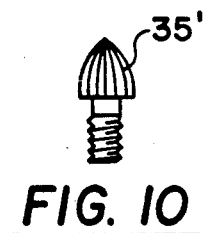

For positioning implants with removable insert, it is possible to use an implant provided, as shown by FIG. 10, with a milling tool 35', which is fixed in the implant instead of in the insert and which passes through the upper cortical area when the implant is positioned, this tool 35' being then unscrewed and replaced by the insert.

Figure 11:
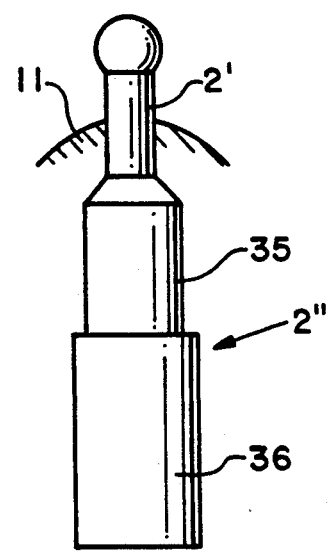

In the embodiment of the invention, such as illustrated by FIG. 11, the part 2" of the body of large cross-section is made in one piece and comprises two cylinders of revolution 35 and 36 which are coaxial and superimposed and the side surfaces of which are smooth or rough. The diameter of the cylinder 36, which is intended to be embedded in the lower portion of the above-mentioned cortical box, is lower than the diameter of the cylinder 35 which is intended to be embedded in the blueberry tissue of the bone.

Due to its cross-section, at least the part 2″ of the implant can be covered with a layer of a biomaterial able to activate the rejuvenation of the osseous material.

As shown by the drawings, the part 2′ of the body 2, intended to be embedded in the upper cortical area 6 has such a length that the implant projects with respect to the gum. This portion 22 of the implant, in projection with respect to the gum, is arranged so as to allow a piece 23 forming part of the implant and which ensures the binding between the latter and a removable prosthesis to be at least temporarily immobilized.

This piece 23 is made of a visco-elastic material, and the implant 1 and the piece 23 are arranged so that the prosthesis freely rests on the gum.

This piece 23 has advantageously a truncated shape, which is substantially coaxial to the body 2, and presents an element 26 of spherical shape bonded to the small base of this piece 23 in order to form a neck 27′ of varying length according to the desired visco-elasticity and the driving-in degree of the prosthesis. The portion 27 of the piece 23, which has a truncated shape, comprises an internal recess 28 in which the free end 22 of the implant projecting in the cavity of the mouth is lodged, so that the piece 23 is retained on this end, while the spherical element 26 is intended to be lodged in the corresponding cavity provided in the prosthesis so as to maintain the latter with respect to the implant.

The bindings between implant 1 and piece 23 and between piece 23 and prosthesis are provided so that, when a pull is exerted on the removable prosthesis, the pieces 23 separate from the implants and remain on the prosthesis. This way of proceeding allows one to easily provide the checkings of the condition of the implant portion and of the gum in the adjacent area of the latter, as well as maintaining this implant portion in a sufficient cleanliness condition.

In order that the implants are acted upon as rarely as possible, the visco-elasticity of the binding pieces 23 is selected so that it is more important than the visco-elasticity of the gum.

It has to be understood that the invention is in no way limited to the described embodiment and that many modifications can be brought thereto without departing from the scope of the following claims.

What is claimed is:

1. A mandibular endosteal implant for a mandible having blueberry tissue enclosed within an endosteum perimetrically defined by bone of a lower cortical area, a lingual cortical area, upper cortical area and a vestibular cortical area, mucosal tissue of a patient's gum intervening between the upper cortical area and a patient's oral cavity, and an opening having a given width and being formed along a generally vertical axis through said mucosal tissue and said upper cortical area into said endosteum, said implant comprising:

a body having a lower portion of a first, larger transverse (relative to said axis) cross-sectional area and a width greater than said given width, said lower portion being arranged to be received in said endosteum and embedded in said blueberry tissue and said lower cortical area, and an upper portion of a second, smaller transverse cross-sectional area projecting upwardly from said lower portion, along said axis, and projecting upwards within said opening to at least a level of flushness with said oral cavity;

said upper portion terminating in an upper end which, when said lower portion is embedded in said lower cortical area, is arranged to be accessible from said oral cavity.

2. The mandibular endosteal implant of claim 1, further including:

a transitional portion of said body disposed axially between said upper portion and said lower portion, said transitional portion being arranged to engage said upper cortical area of said bone marginally of said opening, from within said endosteum.

3. The mandibular endosteal implant of claim 1, wherein:

said upper portion of said body is cylindrically curved about said axis and has a smooth outer peripheral sidewall surface.

4. The mandibular endosteal implant of claim 1, wherein:

said lower portion of said body is cylindrically curved about said axis.

5. The mandibular endosteal implant of claim 4, wherein:

said lower portion has a smooth outer peripheral sidewall surface.

6. The mandibular endosteal implant of claim 4, wherein:

said lower portion has a rough outer peripheral sidewall surface.

7. The mandibular endosteal implant of claim 4, wherein:

said lower portion has an outer peripheral sidewall surface provided with a series of radially outwardly opening circumferential grooves.

8. The mandibular endosteal implant of claim 4, wherein:

said lower portion has an upper region which is arranged to be embedded in said blueberry tissue and has a smooth outer peripheral wall surface having said larger transverse cross-sectional area of at least a given diameter, and a lower region which is arranged to be embedded in said lower cortical area and has a helically threaded outer peripheral wall surface, provided by helical threading having an outer diameter which is larger than said given diameter.

9. The mandibular endosteal implant of claim 8, wherein:

said helically threaded outer peripheral wall surface of said lower region of said lower portion of said body has formed therein a radially outwardly opening generally longitudinal extending groove cutting across said helical threading, and arranged to permit discharge from said endosteum of bone wastes generated by threading said helical threading into said lower cortical area of said bone.

10. The mandibular endosteal implant of claim 8, for a mandible further having a second opening formed through said lower cortical area of said bone into said endosteum along said axis, wherein:

said lower portion further includes, below said helical threading of said lower region, a lower end portion having a wrench-receiving surface means provided thereon and arranged to be accessible within said second opening, for screwing and unscrewing said helically threaded outer peripheral wall surface relative to said lower cortical area.

11. The mandibular endosteal implant of claim 1, wherein:
said lower portion has an upper region which is arranged to be embedded in said blueberry tissue and has a cylindrical outer peripheral wall surface having said larger transverse cross-sectional area of at least a given diameter, and a lower region which is arranged to be embedded in said lower cortical area and has a cylindrical outer peripheral surface having an outer diameter which is larger than said given diameter.

12. The mandibular endosteal implant of claim 1, wherein:
said lower portion is a body of revolution about said axis, which throughout at least a segment of the length thereof has a diameter which is at least as large as the width of said endosteum at a corresponding level, so that said lower portion, when installed, engages said bone between said lingual cortical area and said vestibular cortical area.

13. The mandibular endosteal implant of claim 1, for a mandible further having at least one of a generally horizontal laterally directed opening through said vestibular cortical area and a generally horizontal medially directed opening through said lingual cortical area, further including:
a generally horizontal hole formed through said body; and
a rod arranged to be received in said hole and to project into said at least one generally horizontal opening for pinning said body to said bone.

14. The mandibular endosteal implant of claim 1, wherein:
said body is constituted by two axially adjoining individual elements having a joint located between said upper portion and said lower portion.

15. The mandibular endosteal implant of claim 14, wherein:
said joint is an end-to-end abutment joint arranged to be disposed in use within said blueberry tissue.

16. The mandibular endosteal implant of claim 14, wherein:
said joint is a knuckle joint arranged to be disposed in use within said blueberry tissue.

17. The mandibular endosteal implant of claim 14, wherein:
said joint is an axially made-up pin-in-socket joint.

18. The mandibular endosteal implant of claim 14, wherein:
said joint is a threaded connection.

19. The mandibular endosteal implant of claim 18, wherein:
said threaded connection is constituted by a threaded axial bore formed on said axis in said upper portion, a threaded axial bore formed on said axis in said lower portion, and a screw threaded into both of said axial bores.

20. The mandibular endosteal implant of claim 14, wherein:
both of said elements are made of a like material chosen from the group consisting of titanium, ceramic, carbon, carbonne and gold alloy.

21. The mandibular endosteal implant of claim 1, wherein:
said lower portion of said body has an outer peripheral surface at least partially covered by a layer of a means for actuating rejuvenation of osseous material of said bone.

22. The mandibular endosteal implant of claim 1, further including:
a structure formed on an upper end of said upper portion for securement of a dental prothesis to said body so that said dental prosthesis projects above said gum and into said oral cavity; and
a binding piece mounted to said structure and arranged to engage the patient's gum for immobilizing said structure relative to said gum for facilitating subsequent mounting of said prosthesis to said structure.

23. The mandibular endosteal implant of claim 22, wherein:
said binding piece is made of a viscoelastic material.

24. The mandibular endosteal implant of claim 23, wherein:
said binding piece is mounted to said structure by a ball and socket joint comprising a ball on said structure and a socket in said binding piece; and
said binding piece is arranged to be mounted to a prosthesis by a ball and socket joint comprising a ball on said binding piece.

25. The mandibular endosteal implant of claim 23, for a mandible the overlying gum of which has a given degree of viscoelasticity, wherein:
said binding piece has a viscoelasticity which is greater than said given degree.

* * * * *